United States Patent [19]

Leigh et al.

[11] 4,291,062
[45] Sep. 22, 1981

[54] PHARMACEUTICAL COMPOSITIONS CONTAINING UREA

[75] Inventors: Steven Leigh, South Croydon, England; Peter J. Ayres, Norwich, N.Y.

[73] Assignee: Phares Pharmaceutical Research N.V., Curacao, Netherlands Antilles

[21] Appl. No.: 49,057

[22] Filed: Jun. 15, 1979

[30] Foreign Application Priority Data

Jun. 16, 1978 [GB] United Kingdom .............. 27115/78

[51] Int. Cl.³ ............................................. A61K 31/17
[52] U.S. Cl. .................................... 424/322; 424/59; 424/181; 424/227; 424/230; 424/238; 424/266; 424/273 R; 424/285; 424/301; 424/318; 424/330; 424/346; 424/DIG. 15
[58] Field of Search ........ 424/318, 322, 227, DIG. 15

[56] References Cited

U.S. PATENT DOCUMENTS 3,981,996  9/1976  Leigh .................................. 424/243

OTHER PUBLICATIONS

"Chemistry of Organic Compounds", Noller, 2nd ed., pp. 311–312 (1958).
"Chemical Abstracts 84: 89555q (1926).

*Primary Examiner*—Leonard Schenkman
*Attorney, Agent, or Firm*—Wenderoth, Lind & Ponack

[57] ABSTRACT

Pharmaceutical compositions for application topically or by suppository comprise:
(a) a medicament, preferably protected from degradation by moisture by being presented in small particles of a waxy material,
(b) from 5% to 40% of an inclusion compound of urea with a straight-chain aliphatic compound, preferably a fatty acid or alcohol,
(c) up to 50% of an inert insoluble powder such as starch,
(d) from 25% to 90% of an inert carrier, components (a), (b) and (c) being dispersed in (d).

The compositions have good storage stability and a smooth texture.

8 Claims, No Drawings

PHARMACEUTICAL COMPOSITIONS CONTAINING UREA

This invention relates to pharmaceutical compositions containing urea. It is of particular, though not exclusive, interest in relation to compositions containing medicaments which are sensitive to water. There exist many medicaments, of which tetracycline is an example, which can readily be administered topically, but which are not formulated for topical application because of the short shelf life of the formulations due to the deliberate or accidental presence of small proportions of water.

Urea is well known as an agent for the treatment of hyper-keratotic conditions of the skin. In addition to being of therapeutic value of itself, urea can also act as a hydrating agent by becoming bound to water molecules. In particular, it is capable of hydrating the skin so as to allow the percutaneous transportation of medication, thus acting as a drug delivery system. Furthermore, urea potentiates the action of a wide range of drugs. The use of urea in compositions for topical application has been, however, severely restricted by the fact that urea is unstable in neutral aqueous solution and tends to decompose with the liberation of carbon dioxide and ammonia. One solution to this problem, described in British Patent Specification No. 1,468,815, has been to provide the urea in the form of an aqueous solution adsorbed on particles of a water-soluble powder such as starch which are themselves dispersed in a continuous hydrophobic phase.

It is alternatively possible to use urea in the solid state. Urea is a coarsely crystalline material, and the solid needs to be micronized before incorporation if the resulting composition is not to have a gritty texture. But in the presence of water, even micronized urea rapidly undergoes crystal growth and develops a gritty texture.

It is an object of this invention to provide a pharmaceutical composition for topical application or for use in a suppository which (i) comprises a medicament, particularly one which is sensitive to water, but which nevertheless has good storage stability, and (ii) comprises urea but which nevertheless has a smooth stexture, without the need to rigidly exclude water.

The invention provides a pharmaceutical composition comprising:

(a) an effective concentration of a medicament, (b) from 5% to 40% of small particles of an inclusion compound of urea with at least one straight-chain aliphatic compound having from 4 to 30 carbon atoms per molecule, (c) up to 50% of a powder that is inert to and insoluble in the remaining ingredients, (d) from 25% to 90% of a carrier material which does not dissolve or react with any of components (a), (b) or (c), optionally together with a thickening agent to provide a composition of the desired consistency, components (a), (b) and (c) being dispersed in component (d).

When the medicament is moderately stable to water, for example cortisol, it may be incorporated in finely divided form, together with the urea inclusion compound and the inert powder, in the carrier material. When the medicament is not stable to water, for example tetracycline, or when improved shelf life is desired, it is preferably further protected. Thus component (a) in the above definition is preferably:

(a) from 1% to 30% of small particles of a waxy material containing an effective concentration of the medicament.

In the preparation of component (a) in this form, the medicament is provided in the form of small solid particles preferably having a particle size in the range from 0.1 to 60 microns. The medicament is dispersed in a melt of the waxy material which is then sprayed conveniently by conventional means such as a standard air spray gun, an airless spray gun or by ultrasonic atomization. The spraying preferably takes place within an enclosed chamber where the particles of sprayed suspension congeal to form spheres with the finely divided drug enclosed within the spheres. The average diameter of the spheres preferably falls within the range from 2 to 80 microns, particularly from 10 to 60 microns. The spheres may be used in a wide range of diameters, or if required graded by sieving into a narrow range. The waxy material needs to be one in which the medicament is not soluble. For a polar medicament such as tetracycline hydrochloride, a hydrocarbon wax may be used; for a non-polar medicament such as cortisol, a suitable grade of polyethylene glycol or a vegetable or other wax may be preferred. Since the wax spheres need to be incorporated in a melt of component (d), the wax must have a higher melting point than (d); preferably, the wax melts at a temperature above 37° C.

The stability of the medicament in the composition depends to some extent on the proportion of the medicament in the waxy particles of component (a). A satisfactory proportion of medicament in these particles is from 1% to 30%, particularly 4% to 12% by weight. It has been found particularly advantageous to atomise the waxy material containing the medicament above a stirred reservoir of components (b), (c) and (d), so that the waxy particles congeal and are immediately dispersed in the remainder of the composition in a single step.

It has been well known for many years that urea forms crystalline inclusion compounds with many straight-chain organic compounds having more than 4 carbon atoms, for example hydrocarbons, alcohols, mercaptans, alkylhalides, ketones, acids and esters, but not with branched-chain or cyclic compounds. It appears that the straight-chain compounds are bound to the urea molecules by nothing more than adsorption forces at the solid surface. The chains merely occupy channels in the urea crystal lattice. The melting point of each compound approximates to that of the urea, and the heat of formation is even less than the usual heats of adsorption on solid surfaces. Although each compound is a definite composition, the ratio of urea molecules to straight-chain molecules is not stoichiometric but is proportional to the number of carbon atoms in the chain. Approximately two-thirds of a molecule of urea is combined for each angstrom of chain length.

These inclusion compounds have been used on a commercial scale for many purposes, to improve the octane number of petrol, to lower the freezing point of fuel for jet aircraft and to lower the pour point of lubricating oil by removing the normal hydrocarbons, to isolate and purify compounds and to resolve alkylhalides into optically active components. So far as is known, such inclusion compounds have not been used in pharmaceutical compositions for topical application, and in this area they have two important advantages.

They provide some protection against hydrolysis of urea by small proportions of water that may be present, either deliberately or unavoidably, in the composition. Also, they form small rectangular crystals with rounded ends varying in size from a few microns upwards, whose texture is smooth and non-gritty, so that micronizing before incorporation in pharmaceutical compositions for topical application may be unnecessary. The straight-chain organic compound must be one which is non-toxic and inert to the components (other than urea) of the composition. We prefer to use straight-chain alcohols and, more particularly, carboxylic acids. Specifically, we prefer to use straight-chain fatty acids having from 12 to 18 carbon atoms per molecule such as lauric, palmitic and stearic acids. The use of an acid has the added advantage that the carboxylic acid groups mop up any ammonia which may nevertheless be formed by hydrolysis of the urea.

The inclusion compounds are easily formed. For example, the urea may be partly dissolved in a water or alcohol solvent and added to a melt of the fatty acid or other organic compound. Alternatively, the organic compound may be used in solution, e.g. in alcohol. Alternatively again, the solid urea may be added direct to a melt of the straight-chain organic compound.

The inclusion compound separates as a precipitate of fine particle size. The nature and amount of solvent used can determine to some extent the size of the crystalline particles of inclusion compounds that are formed. The proportions of the components for this reaction are not very critical; the use of quite a small amount of fatty acid helps to stabilise the urea and reduce the crystal size; the presence of an excess of fatty acid is not harmful in the composition; the solvent may be arranged to evaporate off during or after the reaction or to remain in the crystalline compound. We prefer to use a reaction medium containing from 20% to 80%, particularly from 40% to 75%, by weight of urea, from 8% to 75%, particularly from 20% to 40%, by weight of fatty acid or other straight-chain organic compound, and from 0% to 40% by weight of solvent.

A water-insoluble powder is preferably included in the pharmaceutical composition of this invention. The powder helps to mitigate the greasy texture of the composition, and can also assist in ensuring percutaneous absorption of the medicament. The water-insoluble powder is chosen to be inert to the hydrophobic medium and to the medicament, and may be one of the wide range of powders that is conventionally used in pharmaceutical preparations, for example:

(a) polysaccharides such as starch and ethyl cellulose;
(b) silica and inorganic silicates such as talc, kaolin, attapulgite and diatomites;
(c) synthetic polymers such as acrylic, vinyl and phenolic resins;
(d) inorganic materials such as aluminium hydroxide, magnesium hydroxide and calcium phosphate.

It is preferred that the average particle size of the powder should be from 1 micron to 60 microns. While this range is not critical, powders above 30 microns, and more particularly above 60 microns, tend to impart a coarse texture to pharmaceutical compositions, while powders in the sub-micron range are approaching colloidal size and are liable to affect the physical properties of the medium.

The carrier material is chosen to be one which does not dissolve or react with any of components (a), (b) or (c). When component (a) comprises a hydrocarbon wax, the carrier material may be, for example, an oil of vegetable origin, silicone oil or an ester such as di-isopropyl adipate or isopropyl myristate. When component (a) is a polyethylene glycol, then the carrier material may advantageously be a hydrocarbon such as liquid parafin or white soft parafin. Thickeners, for example colloidal silica, bees wax and micro-crystalline wax, may be used as desired. When the composition is intended for topical administration, component (d) should have a softening point of not more than 37° C. When the composition is to be used in the form of a suppository, component (d) may conveniently have a softening point of about 37° C.

A preferred carrier is a blend of glyceryl tribehenate, di-isopropyl adipate and purcellin oil (itself a mixture of cetyl and stearyl octanoates), in proportions to provide the desired viscosity softening point and temperature characteristics. Suitable proportions are glyceryl tribehenate 5 to 20%; di-isopropyl adipate 10 to 40%; and purcellin oil 50 to 85%.

A preferred composition comprises 5 to 15% by weight of component (a) (itself containing 4 to 12% by weight of a dispersed medicament), from 10 to 25% by weight of component (b), from 10 to 30% by weight of component (c) and from 50 to 70% by weight of component (d). Although water is preferably absent, such compositions may tolerate, depending on the medicament used, up to 6% by weight of water. At all events, the amount that can be tolerated without unduly rapid decomposition of the medicament is greater than would be the case if the medicament were not protected by the spray congealing technique.

The nature of the medicament is not critical, and any medicament may be used which is capable of topical application. The invention is of particular advantage, however, in respect of medicaments which are sensitive to water. Examples are:

(a) Corticosteroids and derivatives, for example cortisol and esters thereof, hydrocortisone and the fluorinated corticosteroids, generally in a proportion of from 0.01% to 2% by weight.

(b) Dithranol (anthralin) for the treatment of psoriasis, generally in an amount of from 0.01% to 2% by weight.

(c) Salicylates for the treatment of rheumatic conditions, generally in an amount of from 0.25% to 10% by weight.

(d) Griseofulavin, nystatin, miconazole, tolnaftate, undecanoic acid and related antifungal agents, generally in an amount of from 0.1% to 10% by weight, the undecanoic acid being used either as such or in the form of a urea inclusion compound.

(e) Glycyrrhitinic acid (extract of liquorice) and salts thereof and related anit-inflammatory agents, preferably in an amount of from 0.1% to 10% by weight.

(f) Ephedrine and related vascoconstrictors, preferably in an amount of from 0.05% to 5% by weight.

(g) Vasodilators, for example, nicotinic acid and derivatives, generally in an amount of from 0.1% to 5% by weight.

(h) Antibiotics such as tetracycline erythromycin, clindamycin and salts thereof, generally in an amount of from 0.1% to 5% by weight.

(i) Sun screening preparations comprising mixtures of Vitamins A and D, generally in an amount of from 50,000 to 5,000,000 i.e. per gram.

Pharmaceutical compositions of this invention may be prepared simply by dispersing components (a), (b)

and (c) in a melt of component (d). Obviously, the temperature of the melt must be below the melting point of component (a). Dispersion may be effected by gentle stirring, to avoid disruption of the waxy particles of component (a).

The pharmaceutical compositions of this invention are intended to be applied topically, or by means of a suppository, preferably though not necessarily to skin which is moist. Water, present in or on the skin dissolves the urea and provides a concentrated solution of high osmotic pressure which draws more water through the skin and generally hydrates the skin. The water-insoluble powder serves two purposes. The particles disrupt the waxy spheres when the composition is rubbed into the skin, thus facilitating rapid release of the medicament. The particles also adsorb the concentrated aqueous solution of urea and maintain it in close contact with the stratum corneum. The urea assists solubilization of the medicament, assists its percutaneous transportation, and may in some cases act synergystically and thus potentiate its effect.

There follow descriptions of preparations of urea inclusion compounds. Parts are by weight throughout.

PREPARATION 1

Urea (10 parts) is partially dissolved in a mixture of alcohol (4 parts) and water (2 parts) at about 65° C. and added to stearic acid (4 parts) which has been previously melted at 70° C. The melt is maintained at 62° C. with continuous stirring. An inclusion compound is formed and precipitates. In this example using open vessels the final weight on cooling to room temperature indicates that 3 parts of the solvent has been lost by evaporation. The inclusion compound formed has a smooth feathery texture and microscopically the particles are mainly between 15 and 30 microns across.

PREPARATION 2

This is as Preparation 1, but the alcohol/water mixture is replaced by water (4 parts). Some larger particles which are more plate-like are evident, although the texture remains essentially the same. The melting point, determined on a hot-stage microscope, reveals that the inclusion compound melts at 124° to 126° C. This compares with urea (melting point 132° to 133° C.) and stearic acid (melting point 69° to 70° C.).

PREPARATION 3

This is as Preparation 1, but using urea (10 parts), palmitic acid (4.5 parts) and alcohol (4 parts). In this preparation the alcohol is evaporated off after preparation of the inclusion compound as before. The crystals forming the inclusion compound appear much smaller, while the melting point is around 115° to 116° C. The material is particularly smooth textured.

PREPARATION 4

This is as Preparation 1, but using urea (10 parts), lauric acid (6 parts), and water (5 parts). The inclusion compound formed has more of the waxy characteristics of lauric acid.

PREPARATION 5

This is as Preparation 1, but using urea (10 parts), cetostearyl alcohol (3 parts), and acetone (3 parts). The acetone is lost by evaporation during the preparation. The following Examples illustrate the invention.

EXAMPLE 1

| Component | Percent by Weight |
| --- | --- |
| Wax spheres (10% tetracycline hydrochloride in paraffin wax melting point 65° C.) | 5 |
| Di-isopropyl adipate | 37.6 |
| Urea inclusion compound from Preparation 1 | 15 |
| Starch ether | 40.4 |
| Colloidal silica | 2 |

Tetracycline hydrochloride is micronized to a particle size in the range 1 to 60 microns, and is suspended uniformly in a 10% by weight concentration in molten paraffin wax having a melting point of 65° C. The uniform suspension is sprayed by means of a standard air spray gun and the resulting congealed spheres containing the finely divided tetracycline hydrochloride are then incorporated into a proportion of the di-isopropyl adipate. The starch ether is then added and dispersed. The urea adduct is dispersed, along with the colloidal silica, in the remainder of the di-isopropyl adipate. The two materials are then mixed with gentle stirring to produce the final composition.

EXAMPLE 2

| Compound | Percent by Weight |
| --- | --- |
| Wax spheres (10% cortisol in polyethylene glycol | 10 |
| Isopropyl myristate | 32.5 |
| Urea inclusion compound (Prepn 2) | 25 |
| Starch ether | 32 |
| Polyoxyethylene sorbitan monolaurate | 0.5 |

Cortisol is used either as the free alcohol or as a 17α-hydroxy ester, in a micronized form having a particle size in the range 1 to 60 microns. This material is uniformly suspended in a water-soluble wax, specifically a polyethylene glycol of molecular weight around 4,000. The suspension is then sprayed in a conventional manner and recovered in the form of spheres having an average particle size of 45 to 60 microns. These are dispersed in a proportion of the isopropyl myristate, and the starch ether added. The urea adduct and surfactant are dispersed in the remainder of the isopropyl myristate and the two components mixed to form the final composition.

EXAMPLE 3

| Compound | kg | % |
| --- | --- | --- |
| Tetracycline (as base or hydrochloride) | 0.1 | 0.5 |
| Paraffin wax (mp 60° C.) | 1.9 | 9.5 |
| Urea/Palmitic acid adduct | 3.333 | 16.67 |
| Rice starch ether powder | 3.0 | 15 |
| Lipophilic medium (mixture of higher alcohol esters) | 11.567 | 57.83 |
| Surface active agent | 0.1 | 0.5 |

The tetracycline is vacuum dried to constant weight, and micronised in dry air to a particle size of 1-3 microns (80%). The paraffin wax is heated to 80° C. and the micronised tetracycline dispersed in the melted wax. (Degradation of the tetracycline to anhydro- or epianhydro-tetracycline was not observed to occur under these conditions.) Uniform dispersion of the tetracycline is maintained by high speed stirring of the suspension prior to and during atomisation.

The surfactant is added to the lipophilic medium. The urea adduct is evenly dispersed in a portion of the lipophilic medium with high speed mixing. The rice starch ether powder is evenly dispersed in the remainder of the lipophilic medium and this is then uniformly mixed with the urea adduct dispersion. The blend is cooled to 18° C. and stirring maintained during the formation of tetracycline microspheres.

Atomisation of the tetracycline suspension is effected by means of an ultrasonic velocity transformer. The droplets congeal and fall into the stirred blend of the remaining components where they are rapidly dispersed to form the final composition. Apart from normal drying of the tetracycline, no special drying operations are performed, and no special steps taken to prevent ingress of moisture.

Various samples were prepared by variations of this technique using:

tetracycline as the base or the hydrochloride (HCl)

tetracycline free (F) or protected in waxy microspheres (S)

The tetracycline concentration of these samples was measured, as a percentage of the starting concentration, after storage for 2 and 4 weeks at different temperatures. The results are reported in Table 2.

TABLE 2

Tetracycline Concentration, as a % of original, after Storage

| Tetracycline Compound | Form | Storage Temp. °C. | Storage Time (weeks) 2 | 4 |
|---|---|---|---|---|
| HCl | F | 30 | 53.0 | |
| (TDS 3478) | F | 40 | 52.5 | |
| | F | 45 | 47.9 | |
| Base | F | 30 | 53.1 | |
| (TDS 4478) | F | 40 | 52.5 | |
| | F | 45 | 46.9 | |
| HCl | S | 22 | | 99.7 |
| (TDS 7378) | S | 30 | 95.2 | 95.1 |
| | S | 40 | 100.0 | |
| | S | 45 | 106.0 | |
| Base | S | 22 | | 99.2 |
| (TDS 5838) | S | 30 | 94.0 | 98.6 |
| | S | 40 | 96.0 | |
| | S | 45 | 50.0 | |

EXAMPLES 4, 5, 6, 7

| Compound | % w/w Ex. 4 | Ex. 5 | Ex. 6 | Ex. 7 |
|---|---|---|---|---|
| Part 1 | | | | |
| Poly(ethylene glycol) p-nonylphenol ether | 1.88 | 1.14 | 1.42 | 2.21 |
| Glyceryl tribehenate | 7.50 | 5.69 | 7.11 | 8.82 |
| Di-isopropyl adipate | 15.00 | 11.38 | 14.22 | 17.65 |
| Purcellin oil | 45.00 | 38.64 | 48.30 | 52.94 |
| Corn starch (dried) | 15.00 | 20.00 | — | — |
| Part 2 | | | | |
| Urea/Palmitic acid adduct (micronised) | 14.00 | 23.00 | 28.75 | 16.47 |
| Butylated hydroxyanisole | 0.02 | 0.05 | 0.06 | 0.02 |
| Dithranol | — | 0.10 | 0.12 | — |
| Hydrocortisone | 1.00 | — | — | 1.18 |

To prepare the composition in each case, heat part 1 to 60° C., hold for ½ hour, quick chill and homogenise. Mix parts 1 and 2 until uniform and dispense into tubes.

EXAMPLE 8

| Component | % w/w | |
|---|---|---|
| Poly(ethylene glycol)p-nonylphenol ether | 1.24 | Part 1 |
| Glyceryl tribehenate | 6.20 | Part 1 |
| Di-isopropyl adipate | 12.39 | Part 1 |
| Purcellin oil | 42.15 | Part 1 |
| Corn starch | 15.00 | Part 1 |
| Urea/myristyl alcohol adduct (micronised) | 13.00 | |
| Butylated hydroxyanisole (BHA) | 0.02 | |
| 10% Tetracycline in paraffin wax | 10.00 | |

To prepare the composition, heat part 1 to 60° C., hold for ½ hour, and then quickly chill and homogenise. Then stir in the BHA until uniform, add the urea adduct and stir until homogeneous. Finally spray in the 10% tetracycline in wax as described in Example 3 and mix with low shear mixing.

The tetracycline in this example can be replaced by erythromycin or clindamycin.

We claim:

1. A pharmaceutical composition for application topically or by means of a suppository comprising:

(a) an effective concentration of a medicament for administration topically or by means of a suppository, (b) from 5% to 40% of small particles of an inclusion compound of urea with at least one straight-chain aliphatic compound having from 4 to 30 carbon atoms per molecule, (c) up to 50% of a powder that is inert to and insoluble in the remaining ingredients, (d) from 25% to 90% of a carrier material which does not dissolve or react with any of components (a), (b), or (c), optionally together with a thickening agent to provide a composition of the desired consistency, components (a), (b) and (c) being dispersed in component (d).

2. A composition as claimed in claim 1, wherein component (a) is from 1% to 30% of small particles of a waxy material containing an effective concentration of the medicament.

3. A composition as claimed in claim 2, wherein the small particles have an average diameter of from 10 to 60 microns, are composed of a waxy material which melts at a temperature above 37° C., and contain from 4% to 12% by weight of the medicament.

4. A composition as claimed in claim 1 wherein the aliphatic compound of component (b) is at least one straight-chain fatty acid having from 12 to 18 carbon atoms per molecule.

5. A composition as claimed in claim 1 wherein component (c) is starch having an average particle diameter of from 1 to 60 microns.

6. A composition as claimed in claim 1 wherein component (d) has a softening point below 37° C.

7. A composition as claimed in claim 1 wherein component (d) comprises glyceryl tribehenate 5 to 20%; di-isopropyl adipate 10–40%; and purcellin oil 50 to 85% by weight.

8. A composition as claimed in claim 2 comprising from 5% to 15% by weight of component (a) which itself contains 4% to 12% by weight of a dispersed medicament, from 10% to 25% by weight of component (b), from 10% to 30% by weight of component (c), and from 50% to 70% by weight of component (d).

* * * * *